United States Patent
Snorrason et al.

(10) Patent No.: US 6,358,941 B1
(45) Date of Patent: Mar. 19, 2002

(54) TREATMENT OF ARTHRITIS DISORDERS, RHEUMATOID ARTHRITIS AND MANIFESTATIONS ASSOCIATED WITH RHEUMATOID DISORDERS

(75) Inventors: Ernir Snorrason, Stigahlid 80, 105 Reykjavik (IS); James Murray, Dorfet (GB)

(73) Assignee: Ernir Snorrason, Reykjavik (IS)

( * ) Notice: Subject to any disclaimer, the term of this patent is extended or adjusted under 35 U.S.C. 154(b) by 0 days.

(21) Appl. No.: 09/125,306

(22) PCT Filed: Feb. 19, 1997

(86) PCT No.: PCT/IS97/00001

§ 371 Date: May 3, 1999

§ 102(e) Date: May 3, 1999

(87) PCT Pub. No.: WO97/29750

PCT Pub. Date: Aug. 21, 1997

(30) Foreign Application Priority Data

Feb. 19, 1996 (IS) ........... 4325
Mar. 29, 1996 (GB) ........... 9606736
Apr. 22, 1996 (IS) ........... 4325

(51) Int. Cl.$^7$ ............ A01N 57/18; A61K 31/33; A61K 31/55; A61K 31/40
(52) U.S. Cl. ............ 514/183; 514/141; 514/215; 514/217; 514/410; 514/923
(58) Field of Search ............ 514/183, 141, 514/215, 217, 410, 923

(56) References Cited

U.S. PATENT DOCUMENTS 5,312,817 A 5/1994 Snorrason ............ 514/141
5,360,811 A 11/1994 Tegeler et al. ............ 514/357

OTHER PUBLICATIONS

Bazhenova et al., "Comparative study of some pharmacological properties...", Chemical Abstract, 1970, vol. 72, Abstract # 119889.*

Pavlova, "Influence on Galanthamine...", Chemical Abstract, 1972, vol. 76, Abstract # 135590.*

* cited by examiner

Primary Examiner—Mukund J. Shah
Assistant Examiner—Tamthom N. Truong
(74) Attorney, Agent, or Firm—Raymond J. Lillie

(57) ABSTRACT

The present invention relates to the use of pharmaceutically acceptable cholinesterase inhibitors for the preparation of a pharmaceutical composition for the treatment or prophylaxis of arthritic disorders, including osteoarthritis, rheumatoid arthritis and other rheumatoid diseases such as Juvenile Arthritis, Systemic Lupus Erythematosis, Sjogren's Syndrome, Progressive Systemic Sclerosis, Polymyositis, Dermatomyositis, Ankylosing Spondilitis, Reiter's Syndrome, Psoriatic Arthritis, Relapsing Polychondritis, Relapsing Panniculitis, Crohn's Disease, Ulcerative Colitis, Heredity Complement Deficiencies, Collagen Vascular Diseases, Felty's Syndrome, rheumatological manifestations associated with bacterial and viral endocarditis or myocarditis and other rheumatological manifestations such as anaemia of chronic disorders. The invention also relates to a novel method of treatment or prophylaxis of such diseases and manifestations. Preferably, the cholinesterase inhibitors are selected from a group of nicotinic acetylcholinesterase inhibitors such as galantamine (the name of this drug was previously spelled galanthamine).

29 Claims, No Drawings

TREATMENT OF ARTHRITIS DISORDERS, RHEUMATOID ARTHRITIS AND MANIFESTATIONS ASSOCIATED WITH RHEUMATOID DISORDERS

This application is a continuation of PCT application Ser. No. PCT/IS97/00001, filed Feb. 19, 1997.

SUMMARY OF THE INVENTION

The present invention relates to the use of pharmaceutically acceptable cholinesterase inhibitors of the preparation of a pharmaceutical composition for the treatment or prophylaxis of arthritic disorders, including osteoarthritis, rheumatoid arthritis and other rheumatoid diseases such as Juvenile Arthritis, Systemic Lupus Erythematosis, Sjögren's Syndrome, Progressive Systemic Sclerosis, Polymyositis, Dermatomyositis, Ankylosing Spondilitis, Reiter's Syndrome, Psoriatic Arthritis, Relapsing Polychondritis, Relapsing Panniculitis, Crohn's Disease, Ulcerative Colitis, Hereditary Complement Deficiencies, Collagen Vascular Diseases, Felty's Syndrome, rheumatological manifestations associated with bacterial and viral endocarditis or myocarditis and other rheumatological manifestations such as anaemia of chronic disorders. The invention also relates to a novel method of treatment or prophylaxis of such diseases and manifestations.

Preferably, the cholinesterase inhibitors are selected from a group of nicotinic acetylcholinesterase inhibitors such as galantamine (The name of this drug was previously spelled galanthamine).

DETAILED DESCRIPTION OF INVENTION

In the present description and claims, the term "rheumatoid" covers any of a variety of disorders marked by degeneration or metabolic derangement of the connective tissue structures of the body, especially the joints and related structures, including muscles, bursae (snyovial membranes), tendons and fibrous tissue. They are attended by pain, stiffness, or limitation of motion of these parts. Rheumatoid Arthritis is a chronic, recurrent systemic inflammatory disease primarily of the joints, usually polyarticular, marked by inflammatory changes in the snyovial membranes and articular structures and by atrophy and rarefaction of the bones. In late stages deformity and ankylosis develop. Extra-articular manifestations include vasculitis, atrophy of the skin and muscle, subcutaneous nodules, lymphadenopathy, splenomegaly, leukopaenia and often chronic anaemia.

In one important embodiment of the invention, the arthritic disorder is osteoarthritis. Osteoarthritis is a chronic degenerative disease of skeletal joints, which affects specific joints, commonly knees, hips, hand joints and spine, in adults of all ages. Osteoarthritis is characterized by a number of the following manifestations including degeneration and thinning of the articular cartilage with associated development of "ulcers" or craters, osteophyte formation, hypertrophy of bone at the margins, and changes in the snyovial membrane and enlargement of affected joints. Furthermore, osteoarthritis is accompanied by pain and stiffness, particularly after prolonged activity.

The method of the invention comprises administering an effective amount of a pharmaceutically acceptable cholinesterase inhibitor to a patient in need thereof.

The method of the invention results in the treatment or prevention of one or several of the following symptoms or signs associated with the above-mentioned diseases: muscle pain, muscle weakness, muscle stiffness, joint stiffness, joint pain, joint or tissue swelling, inflammation, and extra-articular manifestation as mentioned above, including anaemia.

The invention is based on discoveries made in connection with the treatment of patients for other conditions, e.g. chronic fatigue syndrome. Surprisingly, it was found that patients who, in addition to fibromyalgia or chronic fatigue syndrome, suffered from osteoarthritis or rheumatoid arthritis, had improvement of their arthritis symptoms.

Thus, ten patients with rheumatoid arthritis were treated with galantamine. The purpose of the treatment was to treat their fatique syndrome resulting from their rheumatoid arthritis. However, it was found that not only did the ten patients improve with respect to their fatique syndrome, but also in the symptoms of their rheumatoid arthritis condition itself. They had less articular pain and the inflammatory process was less active (as evidenced by less swollen and less painful joints) while they were on treatment with galantamine.

In other studies, reported in detail below, patients suffering from rheumatoid arthritis, osteoarthritis and other rheumatoid diseases, respectively, experienced marked improvements of their conditions, e.g. with respect to tiredness, pain, stiffness and grip strength, upon treatment with galantamine.

It was also found by direct measurement that there is a considerable acetylcholinesterase activity in the snyovial fluid of patients with rheumatological conditions. This finding is new and may shed light on the clinical observations with galantamine in rheumatological patients as this acetylcholinesterase activity is believed to exert a proteolytic activity in the snyovial fluid of these patients and may be directly related to tissue damage seen in both rheumatoid diseases and in osteoarthritis.

Patients with rheumatoid diseases or other chronic diseases very often suffer from anaemia of unknown pathophysiology. It is a normochromic, normocytic or hypochromic, non-progressive anaemia—the severity being related to the severity of the chronic disease. Both the serum iron and total iron binding capacity are reduced. The serum ferritin is normal or elevated and bone marrow storage iron is normal but erythroblast iron is reduced. The pathogenesis of this anaemia appears to be related to the decreased release of iron from macrophages, reduced cell lifespan and inadequate erythropoietin response to the anaemia. This anaemia is normally only corrected by successful treatment of the underlying disease and does not respond to iron therapy despite the low serum iron.

Thus, the present invention also relates to the use of pharmaceutically acceptable cholinesterase inhibitors for the preparation of a pharmaceutical composition for treatment or prophylaxis of anaemia associated with chronic disorders.

As appears from the above, the present invention relates to the administration of a cholinesterase inhibiter. Compounds which function as cholinesterase inhibitors may be divided into several groups, namely poison gases for use in warfare, insecticides, such as malathion, and drugs. In the present context, the term "pharmaceutically acceptable" indicates that the cholinesterase inhibitors in question are tolerable for the patient.

Pharmaceutically acceptable cholinesterase inhibitors include, e.g., galantamine and galantamine derivatives, norgalantamine and norgalantamine derivatives, epigalantamine, physostigmine, tacrine and tacrine analogues, fasciculin, metrifonate, heptyl-physostigmine, norpyridostigmine, norneostigmine, and huperzine or a prodrug therefor. Some of the cholinesterase inhibitors show certain undesirable properties, such as short half life, etc. In some cases, such deficiencies can be compensated for by modifying the compound into a prodrug for the active compound, in accordance with well-known principles for prodrug construction, such as introduction of hydrophilic groups to enhance the solubility of a compound in water, thus making it possible to formulate the compound as an injection solution, an introduction of lipophilic groups such as ester groups to enhance the capability of the compound to pass membranes and other barriers of the body to enable the drug to act in the affected area.

The presently preferred cholinesterase inhibitor used according to the invention is galantamine. Galantamine is known as an acetylcholinesterase acting substantially at nicotinic receptor sites, and having a high selectivity for acetylcholinesterase as opposed to butyrylcholinesterase. A more detailed discussion of galantamine and galantamine derivatives is given below:

Galantamine is a well-known acetylcholinesterase inhibitor which is active substantially selectively at nicotinic receptor sites and has substantially little effect on muscarinic receptor sites, is capable of passing the blood-brain barrier in humans, with a good side-effect profile in therapeutically relevant dosages.

Galantamine and acid addition salts thereof have, for many years, been known to have anticholinesterase properties.

Galantamine, a tertiary alkaloid, has been isolated from bulbs of the Caucasian snowdrop, Galanthus woronowi (Proskurnina, N.F. and Yakoleva, A.P. 1952, Alkaloids of Galanthus woronowi. II. Isolation of a new alkaloid. (In Russian.) Zh. Obschchei Khim. (J. Gen. Chem.) 22, 1899–1902. Chem.abs. 47,6959, 1953. It has also been isolated from the common snowdrop Galanthus Nivalis (Boit, 1954).

Galantamine must be considered as being a very desirable drug for the treatment according to the invention of patients suffering from diseases which very often are chronic wherein a life-long treatment may be necessary: The elimination half life of galantamine hydrobromide is over four hours; it shows a practically complete renal elimination. A complete elimination of metabolites and galantamine takes place in 72 hours.

The common side effects, other than the ones related to cholinergic crisis, are either nausea or vomiting, and headache. However, these side effects are uncommon, especially when care is taken to start medication in low doses and then to gradually increase the dose to the optimal active dose such as mentioned above.

The galantamine can suitably be administered orally in the form of an acid addition salt, e.g. the hydrobromide, but other administration forms are possible and realistic, such as described below.

Because galantamine has substantially little effect at muscarinic receptor sites, and shows high selectivity for acetylcholinesterase as opposed to butyrylcholinesterase, it is unlikely to give rise to severe side effects on the heart associated with cholinesterase inhibitors which have a low selectivity. Galantamine has an in vitro selectivity for acetylcholinesterase as opposed to the effect on butyrylcholinesterase of 50 to 1, as reported by Thomsen, Life Sciences, Vol 46, pp. 1553–1558 (1990).

The present invention provides a method of treating or preventing arthritic disorders, including osteoarthritis, rheumatoid arthritis and other rheumatoid diseases such as Juvenile Arthritis, Systemic Lupus Erythematosis, Sjögren's Syndrome, Progressive Systemic Sclerosis, Polymyositis, Dermatomyositis, Ankylosing Spondilitis, Reiter's Syndrome, Psoriatic Arthritis, Relapsing Polychondritis, Relapsing Panniculitis, Crohn's Disease, Ulcerative Colitis, Hereditary Complement Deficiencies, Collagen Vascular Diseases, Felty's Syndrome, rheumatological manifestations associated with bacterial and viral endocarditis or myocarditis and other rheumatological manifestations such as anaemia of chronic disorders, said method comprising administering to a patient in need thereof an effective amount of an acetylcholinesterase such as galantamine, or a derivative of general formula I:

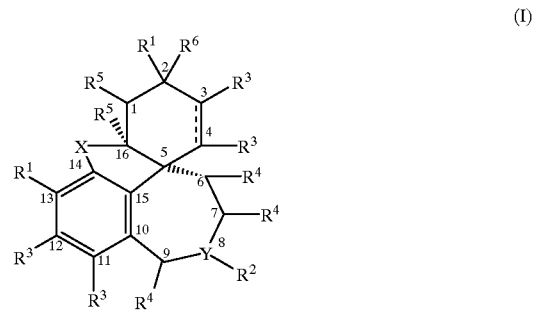

(I)

wherein the broken line represents an optionally present double bond between carbon atoms 3 and 4, each $R_1$ is independently selected from hydrogen, hydroxyl, straight or branched chain alkyl, hydroxyalkyl, carboxyalkyl amino, alkylamino, acyl, lower alkanoyl, cyano, sulfhydryl, $C_{1-6}$alkoxy, alkylthio, aryloxy, arylthio, $R_3$-substituted aryloxy, $R_3$-substituted arylthio, aralkoxy, an optionally $R_3$-substituted aliphatic or aryl carbamyl group, aralkylthio, $R_3$-substituted aralkoxy, $R_3$-substituted aralkylthio, aryloxymethyl, $R_3$-substituted aryloxymethyl, alkanoyloxy, hydroxy-substituted alkanoyloxy, benzoyloxy, $R_3$-substituted benzoyloxy, aryloxycarbonyl and $R_3$-substituted aryloxycarbonyl.

$R_2$ is selected from hydrogen, straight or branched chain $C_{1-6}$alkyl, alkenyl or alkaryl group optionally substituted by a halogen atom or a cycloalkyl, hydroxy, alkoxy, nitro, amino, aminoalkyl, acylamino, heteroaryl, heteroaryl-alkyl, aryl, arylalkyl, cyano, amyl, aroyl, cycloalkylmethyl, allyl, phenyl, $R_3$-substituted phenyl, alkylphenyl, $R_2$-substituted alkylphenyl, heterocyclyl selected from α- or β-furyl, α- or β-thienyl or thenyl, pyridyl, pyrazinyl, and pyrimidyl, alkyl-heterocyclyl or R'-substituted heterocyclyl, where R' is alkyl or alkoxy.

each $R_3$ is independently selected from hydrogen, hydroxyl, sulfhydryl, alkyl, hydroxyalkyl, aryl, aralykyl, alkoxy, mercaptoalkyl, aryloxy, thiaryloxy, alkaryloxy, mercaptoalkaryl, nitro, amino, N-alkylamino, N-arylamino, N-alkarylamino, fluoro, chloro, bromo, iodo, and trifluoromethyl, each $R_4$ is independently selected from hydrogen, halo, trifluoromethyl or $C_{1-4}$-alkyl, each $R_5$ is independently selected from hydrogen or hydroxymethyl, $R_6$ is hydrogen or $C_{1-6}$-alkyl, or when $R_1$ at carbon atom 2 is hydroxyl, $R_6$ may be a moiety of formula I wherein $R_6$ is hydrogen and $R_1$ is a linking bond; or $R_1$ at carbon atom 2 and $R_6$ may jointly form semicarbazone, x is oxygen or $NR_3$, Y is nitrogen or phosphorus, and methylenedioxy derivatives thereof or a pharmaceutically acceptable acid addition salts thereof.

Of the compounds of formula I which may be used in the method of the invention, preferred compounds are those in which the alkyl moieties contain 1 to 8 carbon atoms, halogen atoms are preferably fluoride, bromine, chlorine, aryl moieties are preferably phenyl, cycloalkyl groups are preferably 3- to 7- membered rings, especially cyclopropyl or cyclobutyl, acyl groups are preferably lower alkanoyl groups and heteroaryl moieties are preferably 5- to 8-membered rings, e.g., thienyl, furyl, pyridyl, pyrrolyl, or pyrizanyl.

Preferred compounds of formula I are the compounds of formula II:

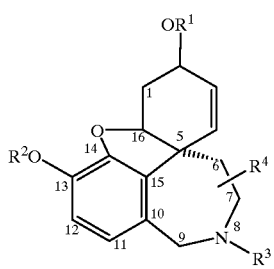

II wherein $R^1$ and $R^2$ which may be the same or different each represents a hydrogen atom or an acyl group, such as a lower alkanoyl group, e.g. an acetyl group or a straight-chained or branched alkyl group, e.g. methyl, ethyl, propyl, or isopropyl;

$R^3$ is a straight or branched chain alkyl, alkenyl or alkaryl group which is optionally substituted by a halogen atom or a cycloalkyl, hydroxy, alkoxy, nitro, amino, aminoalkyl, acylamino, heteroaryl, heteroarylalkyl, aroyl, aroylalkyl or cyano group; and $R^4$ represents a hydrogen or a halogen atom attached to at least one of the ring carbons of the tetracyclic skeleton;

and pharmaceutically acceptable salts thereof, such as a hydrobromide, hydrochloride, methylsulphate or methiodide.

Formula II includes galantamine itself.

Particularly preferred is galantamine itself, and salts thereof such as halides for example galantamine hydrobromide.

Among these compounds are those described in EP-A-236684 and WO88/08708, the disclosures of which are incorporated herein by reference. The derivatives of galantamines of formula I may be prepared by the methods described in these publications.

For use in the method of the invention galantamine and derivatives and salts thereof may be formulated according to conventional methods of pharmacy, together where appropriate with one or more pharmaceutically acceptable carriers, excipients or diluents such as, for example, are described in Remingtons Pharmaceutical Sciences. Such formulations may for example take the form of tablets, capsules, solutions, or lozenges, pessaries, creams, suppositories or transdermal formulations such as patches, depending upon the administration route to be used, which may include enterally or parenterally, including orally or injection via the intravenous, intramuscular or subcutaneous routes.

Oral and transdermal administration routes are preferred.

Precise dosage rates and regimes will depend upon the individual patient and may be determined by the medical practitioner based on individual circumstances. For oral administration doses may be within the range of 1–100 mg per day, such as 2.5 to 70 mg per day; such as 5 to 60 mg, eg. 10 to 30 mg. For transdermal administration galantamine may be delivered in equivalent daily doses. For parenteral administration, dosages may be in the range of 0.1 to 100 mg per day, such as 1 to 100 mg per day, 2.5 to 100 mg per e.g. 5 to 50 mg per day, including 5 to 30 mg per day; lower dosages are often preferred.

Galantamine and its acid addition salts form crystals. They are generally only sparingly soluble in water at room temperature; therefore, injectable compositions are normally in the form of an aqueous suspension. If necessary, pharmaceutically-acceptable suspension aids may be employed. Typically, such a suspension will be employed at a concentration of 0.2–50 mg/ml, such as 1–50 mg/ml, more commonly 5–40 mg/ml, for example, 5–30 mg/ml or 10–40 mg/ml, such as 10–30 mg/ml, especially 20–30 mg/ml of galantamine.

We have found that oral dosages in the range of 10 mg per day result in a distinct improvement in muscle pain and in joint movement.

Viewed from a further aspect, the present invention provides the use of galantamine and derivatives thereof of formula I as hereinbefore defined, and salts thereof, in the manufacture of a medicament for use in the treatment and/or prevention of arthritic disorders, including osteoarthritis, rheumatoid arthritis and other rheumatoid diseases such as Juvenile Arthritis, Systemic Lupus Erythematosis, Sjögren's Snydrome, Progressive Systemic Sclerosis, Polymyositis, Dermatomyositis, Ankylosing Spondilitis, Reiter's Syndrome, Psoriatic Arthritis, Relapsing Polychondritis, Relapsing Panniculitis, Crohn's Disease, Ulcerative Colitis, Hereditary Complement Deficiencies and Collagen Vascular Diseases, Felty's Syndrome, rheumatological manifestations associated with bacterial and viral endocarditis or myocarditis and other rheumatological manifestations such as anaemia of chronic disorders. The invention also relates to a novel method of treatment or prophylaxis of the diseases and manifestations mentioned herein.

The acetylcholinesterase inhibitor, galantamine hydrobromide and its homologues may be administered to patients suffering from Osteoarthrosis, rheumatoid arthritis and other rheumatological diseases orally or by subcutaneous or intravenous injection, transdermal devices or intrathecally by means of an implanted device.

As indicated above, the amount of galantamine is preferably adjusted individually based upon observation of the effects of the initially low dosages. There is a considerable difference with respect to the sensitivity of individuals to acetylcholinesterase inhibitors. Thus, the amount of galantamine is best adjusted by means of a regimen starting at low dosages, e.g. 1 mg, or 2–5 mg, preferably at a dose of 5 mg, per day, but, if appropriate, even as low as 0.1 mg per day. If the dosage is well tolerated by the patient within the first two hours the dosage can be increased to, e.g. 2.5 or 10 mg per dosage, dosed 2, 3 or 4 times per day or in some severe cases to 60 mg or more per day dosed in 2, 3 or 4 divided doses. The preferred doses for long-term treatment are between 10 mg and 30 mg daily, such as 5 mg twice per day, 5 mg 3 times per day, 10 mg twice per day, 10 mg 3 times per day, or 15 mg twice per day. Examples of tablets comprising galantamine are shown in Example 2.

Because cholinergic crisis, a life-threatening dose-dependant side effect associated with all acetylcholinesterase inhibitors, should, by all means, be avoided, it is recommended to start with the low dosages as mentioned above and furthermore not to exceed 150 mg per day and preferably not to exceed dosages above 60 mg per day, unless the patient shows a very low sensitivity to acetylcholinesterase inhibitor, in which case higher doses, such as 200 mg per day, could be used.

The treatment according to the invention should preferably be continued at least until the relevant symptoms have disappeared or have decreased to an acceptable degree. Generally, the treatment should be continued for long periods such as months and years. At relevant intervals, the treatment may be interrupted to see whether the symptoms reappear or not.

While galantamine has, indeed, given remarkable results, such as demonstrated in the clinical cases given in the examples, it is justified to presume that other acetylcholinesterase inhibitors which are functionally similar to galantamine with respect to its combination of high selectivity with respect to nicotinic receptor sites and/or its selectivity for acetyl over butyrylcholinesterase will also show a useful effect against osteoarthritis, rheumatoid arthritis and other manifestations of rheumatoid diseases, and at the same time being acceptable in clinical use, although it cannot be ruled out that galantamine, galantamine salts and galantamine derivatives, due to the special conformation of the galantamine ring system, have specific properties which are decisive for the remarkable effect.

In accordance with the above, compounds which are functionally similar to galantamine are defined herein as compounds which possess an at least 10-fold selectivity, preferably an at least 20-fold selectivity, more preferably an at least 40-fold selectivity, and most preferably an at least 50-fold selectivity, for acetylcholinesterase as opposed to butyrylcholinesterase, when measured by the in vitro method of Thomsen and Kewitz: Selective Inhibition of Human Acetylcholinesterase by Galantamine in vitro and in vivo, Life Sciences, Vol 46, pp. 1553–1558 (1990), and T. Thomsen, H. Kewitz and O. Pleul, J. Clin. Chem. Clin. Biochem. 26 469–475 (1988). The in vitro test described by Thomsen and Kewitz in Life Sciences, Vol 46, pp 1553–1558 (1990) is the one referred to herein whenever numeric (10-fold, 20-fold, 40-fold) reference to selectivity for acetylcholinesterase as opposed to butyrylcholinesterase is made in the claims. According to Thomsen and Kewitz, galantamine hydrobromide, when tested under the conditions described, shows a 50-fold selectivity; this selectivity value is taken as the "fix-point" whenever in vitro selectivities are discussed herein and could be used, for the purpose of determining the selectivities for other cholinesterase inhibitors, as a calibration value which is the one to establish with galantamine hydrobromide in any repetition of the experiment described by Thomsen and Kewitz. Thus, with reference to this determination method, a preferred acetylcholinesterase inhibitor is one which in the in vitro method described has an at least 10-fold selectivity for acetylcholinesterase as opposed to butyrylcholinesterase, such as an at least 20-fold selectivity for acetylcholinesterase as opposed to butyrylcholinesterase, e.g. an at least 40-fold selectivity for acetylcholinesterase as opposed to butyrylcholinesterase.

A relatively easy commercially available selectivity test which can be used as a practical tool in the screening of candidate drugs is the test described in Example 1 herein.

Other preferred compounds according to the present invention include the following acetyl cholinesterase inhibitors: citicoline, donepezil, matrifonate, tacrine, 7-methoxytacrine, eptastigmine, huperzine A and huperzine A analogues, icopezil, ipidacrine, zifrosilone, anseculin, suronacrine, linopirdine, and velnacrine.

The following acetylcholinesterase inhibitors according to the invention are referred to by the code names from the companies from which they are obtainable: OROS oral controlled release drug delivery system of tacrine from Alza and Warner Lambert; SDZ ENA713 from Novartis; NXX 066 from Astra; TAK 147 from Takeda; CHF 2060 from Chiesi; CI 1002 from Parke Davis and Warner Lambert; KW 5092 from Kyowa Hakko; SDZ ENX792 from Novartis; ABS 304 from American Biogenetic Sciences and University of Notre Dame; JWS USC 75IX from Georgia University; ABS 302 from American Biogenetic Sciences and University of Notre Dame; MF 268 from Mediolanum; P 11149 from Hoechst Marion Roussel; P 11467 from Hoechst Marion Roussel; ABS 301 and 303 from American Biogenetic Sciences and University of Notre Dame; SIDR from Strathclyde Institute for Drug Research and Strathclyde University; HP 290 from Hoechst Marion Roussel and Astra; and SM 10888 from Sumitomo. In addition the transdermal drug delivery system of physostigmine from Pharmetrix and Pharma Patch and phenserine from the National Institute of Health are suitable pharmaceutical formulations according to the invention.

According to a further aspect of the invention, acetyl cholinesterase inhibitors described in International Publication No. WO 93/07140 are considered to be effective in the treatment and prophylaxis of the present invention and include as follows:

1-(2-methyl-1H-benzimidazol-5-yl)-3-[1-(phenylmethyl)-4-piperidinyl]-1-propanone;
1-(2-phenyl-1H-benzimidazol-5-yl)-3-[1-(phenylmethyl)-4-piperidinyl]-1-propanone;
1-(1-ethyl-2methyl-1H-benzimidazol-5-yl)-3-[1-(phenylmethyl)-4-piperidinyl]-1-propanone;
1-(2-methyl-6-benzothiazolyl)-3-[1-(phenylmethyl)-4-piperidinyl]-1-propane;
1-(2-methyl-6-benzothiazolyl)-3-[1-[(2-methyl-4-thiazolyl)-methyl]-4-piperidinyl]-1-propanone;
1-(5-methyl-benzo[b]thien-2-yl)-3-[1-(phenylmethyl)-4-piparidinyl]-1-propanone;
1-(6-methyl-benzo[b]thien-2-yl)-3-[1-(phenylmethyl)-4-piperidinyl]-1-propanone;
1-(3, 5-dimethyl-benzo[b]thien-2-yl)-3-[1-(phenylmethyl)-4-piperidinyl]-1-propanone;
1-(benzo[b] thien-2yl)-3-[1-(phenylmethyl)-4-piperidinyl]-1-propanone;
1-(benzofuran-2-yl)-3-[1--(phenylmethyl)-4-piperidinyl]-1-propanone;
1-(1-phenylsulfonyl-6-methyl-indol-2-yl)-3-[1-(phenylmethyl)-4-piperidinyl]-1-propanone;
1-(6-methyl-indol-2-yl)-3-[1-(phenylmethyl)-4-piperidinyl]-1-propanone;
1-(1-phenylsulfonyl-5-amino-indol-2-yl)-3-[1-(phenylmethyl)-4-piperidinyl]-1-propanone;
1-(5-amino-indol-2-yl)-3-[1-(phenylmethyl)-4-piperidinyl]-1-propanone;
1-(5-acetylamino-indol-2-yl)-3-[1-(phenylmethyl)-4-piperidinyl]-1-propanone;
1-(6-quinolyl)-3-[1-(phenylmethyl)-4-piperidinyl]-1-propanone;
1-(5-indolyl)-3-[1-(phenylmethyl)-4-piperidinyl]-1-propanone;
1-(5-benzthienyl)-3-[1-(phenylmethyl)-4-piperidinyl]-1-propanone;
1-(6-quinazolyl)-3-[1-(phenylmethyl)-4-piperidinyl]-1-propanone;
1-(6-benzoxazolyl)-3-[1-(phenylmethyl)-4-piperidinyl]-1-propanone;

1-(5-benzofuranyl)-3-[1-(phenylmethyl)-4-piperidinyl]-1-propanone;
1-(5-methyl-benzimidazol-2-yl)-3-[1-(phenylmethyl)-4-piperidinyl]-1-propanone;
1-(6-methyl-benzimidazol-2-yl)-3-[1-(phenylmethyl)-4-piperidinyl]-1-propanone;
1-(5-chloro-benzo[b]thien-2-yl)-3-[1-(phenylmethyl)-4-piperidinyl]-1-propanone;
1-(5-azaindol-2-yl)-3-[1-(phenylmethyl)-4-piperidinyl]-1-propanone;
1-(6-azabenzo[b]thien-2-yl)-3-[1-(phenylmethyl)-4-piperidinyl]-1propanone;
1-(1H-2-oxo-pyrrolo[2', 3', 5, 6]benzo[b]thieno-2-yl)-3-[1-(phenylmethyl)-4-piperidinyl]-1-propanone;
1-(6-methyl-benzothiarol-2-yl)-3-[1-(phenylmethyl)-4-piperidinyl]-1-propanona;
1-(6-methoxy-indol-2-yl)-3-[1-(phenylmethyl)-4-piperidinyl]-1-propanone;
1-(6-methoxy-benzo [b]thien-2-yl)-3-[1-(phenylmethyl)-4-piperidinyl]-1-propanone;
1-(6-acetylamino-benzo[b]thien-2-yl)-3-[1-(phenylmethyl)-4-piperidinyl]-1-propanone; and
1-(5-acetylanino-benzo[b]thien-2-yl)-3-[1-(phenylmethyl)-4-piperidinyl]-1-propanone.
1-(5-acetylamino-benzo[b]thien-2-yl)-3-[1-(phenylmethyl)-4-piperidinyl]-1-propanone.

The invention will now be described with reference to the following non-limiting Examples.

EXAMPLE 1

Test for Cholinesterase Activity in Blood Samples

Method

SIGMA DIAGNOSTICS® CHOLINESTERASE (PTC) kit, available from Sigma Diagnostics, can be used for determining the activity and selectivity of cholinesterase inhibitors. In the following, it is illustrated how the kit is used for the determination of the activity and selectivity of galantamine hydrobromide.

Reactions involved in the cholinesterase assay are as follows:

$$\text{Propionylthiocholine} + H_2O \xrightarrow{\text{esterase}} \text{Propionic Acid} + \text{Thiocholine}$$

Thiocholine+5, 5'-Dithiobis-2-Nitrobenzoic Acid→5-Thio-2-Nitrobenzoic Acid

5-Thio-2-Nitrobenzoic Acid is assessed by measuring the absorbance at 405 nm. The rate of change in absorbance at 405 nm is directly proporational to cholinesterase activity.

The activity of erythrocyte cholinesterase may be calculated on the basis of the measurement of butyrylcholinesterase (pseudocholinesterase) in serum and cholinesterase in haemolyzed whole blood (haemolysate), both measured simultaneously by the method described above, and evaluated according to the haematocrit value according to the formula $$HChE=(EChE \times Hctg^*)+(PChE \times (1-Hct^*))$$

Therefore, $EChE = \dfrac{HChE - (PChE \times (1 - Hct^*))}{Hct^*}$

*Haematocrit value expressed as decimal equivalent (i.e., 44% = 0.44).

In the above formulae, EChE is erythrocyte cholinesterase activity, PChE is plasma cholinesterase activity, HChE is haemolysate cholinesterase activity, and Hct is haematocrit value of the sample.

Another way of assessing the cholinesterase activity is to measure the plasma cholinesterase and the cholinesterase in purified haemolyzed erythrocytes. By doing this, the values are obtained directly.

Blood samples from 3 patients were tested with the Sigma test. The tests were carried out with samples where no galantamine was added and with samples where 1.25 μg/ml galantamine and 2.5 μg/ml were added in vitro. The results are shown below in table 1.1.

TABLE 1.1

| Galantamine added μg/ml | Haemolysate ChE activity | Serum ChE activity |
|---|---|---|
| 0 | 1.00 | 1.00 |
| 1.25 | 0.96 | 0.98 |
| 2.50 | 0.86 | 0.97 |

The results show a significant reduction of the haemolysate cholinesterase activity with increased concentration of galantamine hydrobromide, whereas the data for the serum activity do not show any statistically significant changes as a response to the addition of the galantamine hydrobromide, which is an indication of a high selectivity of the galantamine hydrobromide with respect to acetylcholinesterase as opposed to butyrylcholinesterase.

Selectivity for acetylcholinesterase in erythrocytes opposed to butyrylcholinesterase is contemplated to reflect the selectivity for acetylcholinesterase at nicotinic receptor sites opposed to the acetylcholinesterase at muscarinic receptor sites.

This test may be used as a screening for candidate cholinesterase inhibitors with respect to their selectivity. However, other test may be used.

EXAMPLE 2

| Formulations of tablets containing 1 mg galantamine |  |
|---|---|
| Composition of 1 tablet containing 1 mg galantamine |  |
| Galantamine hydrobromide | 0.001 g |
| Calcium phosphate | 0.032 g |
| Lactose | 0.005 g |
| Wheat Starch | 0.0056 g |
| Microcrystalline Cellulose | 0.015 g |
| Talc | 0.0007 g |
| Magnesium Stearate | 0.0007 g |
| Composition of 1 tablet containing 5 mg galantamine |  |
| Galantamine hydrobromide | 0.005 g |
| Calcium phosphate | 0.024 g |
| Lactose | 0.004 g |
| Wheat Starch | 0.004 g |
| Microcrystalline Cellulose | 0.04 g |

-continued

Formulations of tablets containing 1 mg galantamine

| | |
|---|---|
| Talc | 0.002 g |
| Magnesium Stearate | 0.001 g |
| Composition of 1 tablet containing 10 mg galantamine | |
| Galantamine hydrobromide | 0.010 g |
| Lactose | 0.040 g |
| Wheat Starch | 0.0234 g |
| Microcrystalline Cellulose | 0.0374 g |
| Talc | 0.0036 g |
| Magnesium Stearate | 0.0012 g |
| Gelatin | 0.0044 g |

Preparation

All the tablets are prepared according to routine tablesetting procedures.

EXAMPLE 3

Acetylcholinesterase Activity in Snyovial Fluid

Acetylcholinesterase (AcChE) activity was determined in snyovial fluid from 8 patients with osteoarthritis (OA) and 5 subjects with different Rheumatoid conditions. In each patient snyovial fluid was taken from an affected joint by arthrocentesis. Table 3.1 shows mean values of up to six samples from individual subjects. A broad spectrum of values was seen between these patients, but with a high degree of correspondence between samples taken on different days from the same patient. Samples with high values show bands with AcChE activity on isoelectric focusing gels. It seems that this acetylcholinesterase activity is from free proteins rather than membrane bound simply because of the parsity of lymphocytes seen in the microliter samples.

TABLE 3.1

| Subject | Age (years) | Condition | AcChE | N | SEM |
|---|---|---|---|---|---|
| 1 (KJ) | 70 | OA | 16.9 | 3 | 3.08 |
| 2 (SA) | 67 | RA | 9 | 1 | — |
| 3 (GS) | 74 | OA | 9.6 | 1 | — |
| 4 (SG) | 88 | OA | 7.1 | 1 | — |
| 5 (SR) | 41 | Menisc | 2.1 | 2 | 1.15 |
| 6 (BG) | 50 | Menisc | 28.9 | 2 | 3.95 |
| 7 (PJ) | 71 | OA | 3.9 | 2 | 1.45 |
| 8 (SE) | 31 | Menisc | 22.8 | 1 | — |
| 9 (GV) | 75 | OA | 6.63 | 5 | 6.63 |
| 10 (SE) | 73 | OA | 0.71 | 3 | 0.71 |
| 11 (GA) | 58 | Hydrops | 3.7 | 2 | 3.7 |
| 12 (AL) | 70 | OA | 1.53 | 6 | 1.53 |
| 13 (SO) | 54 | OA | 23.4 | 1 | — |
| 14 (HG) | 62 | OA | 4.07 | 3 | 4.07 |

Patient numbers 1, 3, and 11 are males, the remaining patients are females.

In patient numbers 1, 6, 7, 11, and 14 samples were taken from the left knee. As for the remaining patients, samples were taken from the right knee.

AcChE=Acetylcholinesterase activity
N=number of measurements
SEM=Standard Error of the Means
OA=Osteoarthritis
RA=Rheumatoid Arthritis
Menisc=Lesion of the meniscus
Hydrops=Swollen knee

EXAMPLE 4

Treatment of patients with rheumatoid disease

Ten patients with rheumatoid arthritis were treated with galantamine 10 mg 3 times per day. The purpose of the treatment was to treat their fatigue syndrome resulting from their rheumatoid arthritis. However, it was found that not only did the ten patients improve with respect to their fatigue syndrome, but also in respect of the symptoms of their rheumatoid arthritis condition itself. They spontaneously reported less articular pain and the inflammatory process of their affected joints was less active (as evidenced by less swollen and less painful joints) while they were on treatment with galantamine. Most of the patients have experienced relapse of their symptoms when treatment was interrupted.

EXAMLE 5

Treatment of Patients with Osteoarthritis

In a bioavailability study of galantamine in 24 elderly volunteers, 2 volunteers asked to remain on galantamine at the end of the trial.

The first volunteer, who was already acknowledged by the General Practitioner to be suffering from osteoarthritis, received 10 mg galantamine hydrobromide per day (in the form of 2=5 mg doses orally). After seven days, the patient spontaneously reported an improvement in osteoarthritis symptoms. This improvement was maintained over a 31 day period, during which the galantamine hydrobromide dose was raised to 30 mg per day. Symptoms were reported to recur when medication was discontinued.

The second patient who has been experiencing joint pain for several years, but had not had osteoarthritis diagnosed, also received 10 mg per day galantamine hydrobromide in 2=5 mg tablet doses. This patient spontaneously reported an improvement in symptoms after three days.

EXAMPLE 6

Treatment of a Patient with Anaemia of Chronic Disorder

A 61 years old woman with Rheumatoid Arthritis had for 3 years suffered from anaemia which did not respond to conventionally therapy.

The patient received 15 mg galantamine hydrobromide per day (in the form of 3=5 mg doses orally). After 14 days, the laboratory blood tests reflecting anaemia showed significant improvement as shown in Table 6.1. The patient was treated in the period between Jan. 3, 1997 and Jan. 20, 1997.

TABLE 6.1

| Normal values | 2-12-96 | 3-1-97 | 20-1-97 |
|---|---|---|---|
| White cells 3.8–10.2 × $10^9$/L | 6.1 | 6.6 | 5.9 |
| Red cells: 4.00–5.8 × $10^{12}$/L | 3.81* | 3.72* | 3.94 |
| Haemoglobin: 118–158 g/L | 118 | 115* | 124 |
| Haematocrit: 0.360–0.470 L/L | 0.362 | 0.342* | 0.362 |
| MCV: 1.0-96.0 fl | 95.0 | 91.8 | |
| MCH: 26.5–32.4 pg | 31.1 | 30.9 | |
| MCHC: 323–351 | 327 | 336 | |

TABLE 6.1-continued

| Normal values | 2-12-96 | 3-1-97 | 20-1-97 |
|---|---|---|---|
| RDW: 10.9–15.7 | 13.25 | 12.4 | |
| Platelet: 130–370 | 266 | 283 | |

Two weeks' treatment with galantamine 15 mg per day apparently raised haemoglobin to 124, the highest value in three years, and also improved considerably other clinical signs and symptoms.
*= abnormal values

EXAMPLE 7

Treatment of Patients with Rheumatoid Diseases 13 patients suffering from different arthritic disorders of rheumatoid origin received galantamine tablets 2.5 mg 3 times per day for 1 week followed by 5 mg 3 times per day for the next four weeks. After the 5 weeks of treatment the patients reported the following differences in symptoms as shown in Table 7.1.

TABLE 7.1

Tab. Galantamine HBr, 5 mg
Effect in patients with rheumatological diseases

| Subject | Age | Condition | Pain | Concentration | Memory | Stiffness |
|---|---|---|---|---|---|---|
| 1 (EB) | 60 | RA | d | u | u | d |
| 2 (GT) | 63 | OA | d | i | i | d |
| 3 (GA) | 34 | OA (mild) | d | i | i | u |
| 4 (GG) | 40 | Post. inf. a. | u | u | u | u |
| 5 (GR) | (50?) | SLE | d | u | u | |
| 6 (GS) | (40?) | Spond | u | u | u | u |
| 7 (IG) | 48 | Spond | u | u | u | u |
| 8 (MG) | 52 | Spond | u | u | u | u |
| 9 (RB) | 60 | Poly/RA | d | u | u | u |
| 10 (SEB) | 39 | Poly/RA | d | u | u | u |
| 11 (SO) | 62 | Poly | u | u | u | u |
| 12 (PT) | 30 | Pso. a. | d | i | i | d |
| 13 (UJ) | 60 | Poly | u | | | u |

Patient numbers 4 and 12 are males, the remaining patients are females. Age is measured in years, age in brackets reflect approximate age.

OA=Osteoarthritis
RA=Rheumatoid Arthritis
Post inf. a.=Arthritis after infection
SLE=Systematic Lupus Erythematosis
Spond=Ankylosing Spondilitis
Poly=Polyarthritis
Pso. a. =Arthristis associated with psoriasis
u=unaffected
d=decreased
i=increased (corresponding to at least 50% improvement)

Stiffness: Joint stiffness is a complaint covering sensations which range from slight resistance to all movements through the normal range, to blocking of certain movements due to fixed anatomical changes. Certain types of stiffness are highly characteristic, such as early morning stiffness.

Early morning stiffness occurs primarily in rheumatoid arthritis, but also in other arthritic diseases. The patient awakes with distressing, painful stiffness of all affected joints. This is gradually "worked off " by activity over one half to three hours or more. This "limbering up time" provides a reliable measure of inflammatory activity. In osteoarthritis stiffness tends to come on later in the day and is preceded by activity.

In one of the examples given of rheumatoid patients on galantamine, the parameters evaluated were tiredness, sleep, pain, and stiffness. In one RA patient (patient number 1) the grip strength was evaluated and proved to augment over 50%. All these parameters were evaluated with a questionaire and VAS (Visual Analogue Scale) which refer to the patients' reporting as regards the severity of the symptoms, represented by a 0–100 percentage line.

As appears from Table 7.1, 50% of the patients (patient numbers 1, 2, 3, 5, 9, 10, and 12) reported a significant improvement in their symptoms.

What is claimed is:

1. A method of treatment of an arthritic disorder, or a rheumatoid disease associated therewith wherein the rheumatoid disease is selected from the group consisting of systemic lupus erythematosis, psoriatic arthritis and chronic anemia, comprising administering to a patient an effective amount of galantamine, a galantamine compound or a salt thereof, wherein said galantamine, galantamine derivative, or salt thereof has the general formula I:

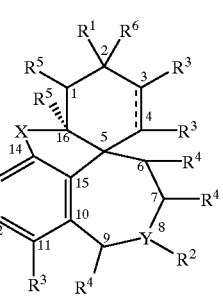

wherein the broken line represents an optionally present double bond between carbon 3 and 4, each $R_1$ is independently selected from hydrogen, hydroxyl, straight or branched chain alkyl, hydroxyalkyl, carboxyalkyl amino, alkyiamino, acyl, lower alkanoyl, cyano, sulfhydryl, $C_{1-6}$alkoxy, aryloxy, arylthio, $R_3$-substituted aryloxy, $R_3$-substituted arylthio, aralkoxy, an optionally $R_{-3}$ substituted aliphatic or aryl carbarnyl group, aralkylthio, $R_3$-substituted aralkoxy, $R_3$ substituted aralkylthio, aryloxymethyl, $R_3$-substituted aryloxymethyl, alkanoyloxy, hydroxy-substituted alkanoyloxy, benzoyloxy, $R_3$-substituted benzoyloxy, aryloxycarbonyl, and $R_3$-substituted aryloxycarbonyl, $R_2$ is selected from hydrogen, straight or branched chain $C_{1-6}$ alkyl, alkenyl or alkaryl group optionally substituted by a halogen atom or a cycloalkyl, hydroxy, alkoxy, nitro, amino, aminoalkyl, acylamino, heteroaryl, heteroaryl-alkyl, aryl, arylalkyl, cyano, amyl, aroyl, cycloalkylmethyl, allyl, phenyl, $R_3$-substituted phenyl, alkylphenyl, $R_3$-substituted alkylphenyl, heterocyclyl selected from α- or β-furyl, α- or β-thienyl or thenyl, pyridyl, pyrazinyl, and pyrimidly, alkylheterocyclyl or R'-substituted heterocyclyl, where R' is alkyl or alkoxy, each $R_3$ is independently selected from hydrogen, hydroxyl, sulfhydryl, alkyl, hydroxyalkyl, aryl, aralkyl, alkoxy, mercaptoalkyl, aryloxy, thiaryloxy, alkaryloxy, mercapto-alkaryl, nitro, amino, N-alkylamino, N-arylamino, N-alkarylamino, fluoro, chloro, bromo, iodo, and trifluoromethyl, each $R_4$ is independently selected from hydrogen, halo, trifluoromethyl or $C_{1-4}$-alkyl, each $R_5$ is independently selected from hydrogen or hydroxymethyl, $R_6$ is hydrogen or $C_{1-6}$-alkyl, or when $R_1$ is hydroxyl, $R_6$ may be a moiety of formula I wherein $R_6$ is hydrogen and $R_1$ is a linking bond; or $R_1$ and $R_6$ may jointly form semicarbazone, X is oxygen or $NR_3$, Y is nitrogen or phosphorus, and pharmaceutically acceptable acid addition salts thereof.

2. The method of claim 1 wherein the arthritic disorder is rheumatoid arthritis.

3. The method of claim 1 wherein the arthritic disorder is osteoarthritis.

4. The method of claim 1, in which the acetylcholinesterase inhibitor is galantamine or a galantamine compound having the general formula II

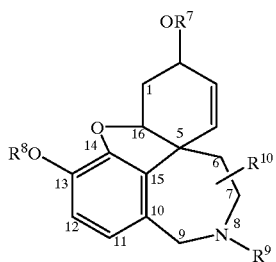

wherein $R^7$ and $R^8$ which may be the same or different and each of $R^7$ and $R^8$ is a hydrogen atom or an acyl group, or a straight-chained or branched alkyl group;

$R^9$ is a straight or branched chain alkyl, alkenyl or alkaryl group which is optionally substituted by a halogen atom or a cycloalkyl, hydroxy, alkoxy, nitro, amino, aminoalkyl, acylamino, heteroaryl, heteroarylalkyl, aroyl, aroylalkyl or cyano group; and $R^{10}$ represents a hydrogen or a halogen atom attached to at least one of the ring carbons of the tetracyclic skeleton, and pharmaceutically acceptable salts thereof.

5. The method of claim 4 wherein said acyl group is a lower alkanoyl group.

6. The method of claim 5 wherein said lower alkanoyl group is an acetyl group.

7. The method of claim 4 wherein said straight-chained or branched alkyl group is selected from the group consisting of methyl, ethyl, propyl, and isopropyl.

8. The method of claim 4 wherein said pharmaceutically acceptable salt is selected from the group consisting of hydrobromide salts, hydrochloride salts, methylsulfate salts, and methiodide salts.

9. The method of claim 1, wherein the galantamine, galantamine compound, or salt thereof is galantamine hydrobromide.

10. The method of claim 1, wherein the galantamine, galantamine compound, or salt thereof is administered in the form of a pharmaceutical composition which is a tablet, a capsule, a sustained release capsule comprising microcapsules of the active ingredient, a solution or suspension, a device for transdermal application, or a suppository or implant.

11. The method of claim 1, in which the galantamine, galantamine compound, or salt thereof is administered parenterally at a dosage which is from with 0.1 to 1,000 mg of galantamine hydrobromide per day.

12. The method of claim 11 wherein the galantamine, galantamine compound, or salt thereof is administered parenterally at a dosage which is from with 1 to 500 mg of galantamine hydrobromide per day.

13. The method of claim 12 in which the galantamine, galantamine compound, or salt thereof is administered parenterally at a dosage which is from with 5 to 300 mg of galantamine hydrobromide per day.

14. The method of claim 13 wherein the galantamine, galantamine compound, or salt thereof is administered parenterally at a dosage which is from with 7.5 to 100 mg of galantamine hydrobromide per day.

15. The method of claim 14 in which the galantamine, galantamine compound, or salt thereof is administered parenterally at a dosage which is from with 10 to 60 mg of galantamine hydrobromide per day.

16. The method of claim 15 wherein the galantamine, galantamine compound, or salt thereof is administered parenterally at a dosage which is from with 10 to 30 mg of galantamine hydrobromide per day.

17. The method of claim 1 wherein the galantamine, galantamine compound, or salt thereof is administered orally at a dosage which is from with 1 to 1000 mg of galantamine hydrobromide per day.

18. The method of claim 17 wherein the galantamine, galantamine compound, or salt thereof is administered orally at a dosage which is from with 2.5 to 500 mg of galantamine hydrobromide per day.

19. The method of claim 18 wherein the galantamine, galantamine compound, or salt thereof is administered at a dosage which is from with 5 to 300 mg of galantamine hydrobromide per day.

20. The method of claim 19 wherein the galantamine, galantamine compound, or salt thereof is administered orally at a dosage which is from with 5 to 100 mg of galantamine hydrobromide per day.

21. The method of claim 20 in which the galantamine, galantamine compound, or salt thereof is administered at a dosage which is from with 5 to 60 mg of galantamine hydrobromide per day.

22. The method of claim 21 wherein the galantamine, galantamine compound, or salt thereof is administered orally at a dosage which is from with 7.5 to 30 mg of galantamine hydrobromide per day.

23. The method of claim 1 in which the galantamine, galantamine compound, or salt thereof is active substantially selectively at nicotinic receptor sites.

24. The method of claim 1 in which the galantamine, galantamine compound, or salt thereof has an at least 10-fold selectivity for acetylcholinesterase as opposed to butyrylcholinesterase.

25. The method of claim 24 in which the galantamine, galantamine compound, or salt thereof has an at least 20-fold selectivity for acetylcholinesterase as opposed to butyrylcholinesterase.

26. The method of claim 25 in which the galantamine, galantamine compound, or salt thereof has an at least 40-fold selectivity for acetylcholinesterase as opposed to butyrylcholinesterase.

27. The method of claim 1 in which the galantamine, galantamine compound, or salt thereof, upon administration in an amount of 10 mg to a healthy adult, results in inhibition of at least 40% of the acetylcholinesterase activity in erythrocytes from the adult and no substantial inhibition of butyrylcholinesterase therein.

28. The method of claim 27 in which the galantamine, galantamine compound, or salt thereof when administered in an amount of 10 mg to a healthy adult, results in inhibition of at least 50% of the acetylcholinesterase activity in erythrocytes from the adult.

29. The method of claim 1 in which the galantamine, galantamine compound, or salt thereof is capable of passing the blood-brain barrier in humans.

* * * * *